(12) United States Patent
Liu et al.

(10) Patent No.: US 11,459,402 B2
(45) Date of Patent: Oct. 4, 2022

(54) **HYBRIDOMA CELL STRAIN AND MONOCLONAL ANTIBODY PRODUCED THEREFROM AGAINST SERINE PROTEASE OF *TRICHINELLA SPIRALIS* IN INTESTINAL STAGE AND APPLICATION THEREOF**

(71) Applicant: Jilin University, Changchun (CN)

(72) Inventors: Mingyuan Liu, Changchun (CN); Xiaolei Liu, Changchun (CN); Yong Yang, Changchun (CN); Xuelin Wang, Changchun (CN); Xue Bai, Changchun (CN); Bin Tang, Changchun (CN); Jing Ding, Changchun (CN)

(73) Assignee: JILIN UNIVERSITY, Changchun (CN)

( * ) Notice: Subject to any disclaimer, the term of this patent is extended or adjusted under 35 U.S.C. 154(b) by 112 days.

(21) Appl. No.: 17/111,608

(22) Filed: Dec. 4, 2020

(65) Prior Publication Data

US 2021/0155714 A1 May 27, 2021

(30) Foreign Application Priority Data

Jan. 21, 2020 (CN) .......................... 202010071584.7

(51) Int. Cl.
*C12N 1/20* (2006.01)
*C07K 16/40* (2006.01)
*G01N 33/577* (2006.01)
*A61K 39/00* (2006.01)

(52) U.S. Cl.
CPC ........... *C07K 16/40* (2013.01); *G01N 33/577* (2013.01); *A61K 39/00* (2013.01); *C07K 2317/14* (2013.01); *G01N 2333/95* (2013.01); *G01N 2800/26* (2013.01)

(58) Field of Classification Search
None
See application file for complete search history.

(56) References Cited

U.S. PATENT DOCUMENTS 4,670,384 A    6/1987 Gamble et al.

*Primary Examiner* — Jennifer E Graser
(74) *Attorney, Agent, or Firm* — IPRO, PLLC; Na Xu (57) ABSTRACT

A hybridoma cell stain and a monoclonal antibody secreted therefrom and application thereof belong to the technical field of prevention and treatment of *Trichinella spiralis* (*T. spiralis*). Aiming at the technical problem of how to specifically diagnose trichinellosis, the disclosure provides a hybridoma cell strain deposited under an accession number of CGMCC No. 18317. Tests show that the monoclonal antibody Ts-ZH68-2A4-Ab secreted by the hybridoma cell strain can compete with the positive serum of pigs infected with *T. spiralis* for binding to Ts-ZH68 antigen, and the recognition peptide is $^{222}$GVDRSATCQGDSGGP$^{236}$. The monoclonal antibody of the disclosure and the Ts-ZH68 protein B cell epitope polypeptide recognized by the monoclonal antibody can be used to prepare a reagent or a vaccine for diagnosing or preventing infection of *T. spiralis*, laying the foundation for establishment of a serological diagnosis method of *T. spiralis*.

4 Claims, 4 Drawing Sheets
Specification includes a Sequence Listing.

SEQUENCE LISTING

```
<160> NUMBER OF SEQ ID NOS: 18

<210> SEQ ID NO 1
<211> LENGTH: 15
<212> TYPE: PRT
<213> ORGANISM: Artificial sequence
<220> FEATURE:
<223> OTHER INFORMATION: Translated from synthetic DNA

<400> SEQUENCE: 1

Gly Val Asp Arg Ser Ala Thr Cys Gln Gly Asp Ser Gly Gly Pro
1               5                   10                  15

<210> SEQ ID NO 2
<211> LENGTH: 19
<212> TYPE: PRT
<213> ORGANISM: Artificial sequence
<220> FEATURE:
<223> OTHER INFORMATION: Translated from synthetic DNA

<400> SEQUENCE: 2

Tyr Asn Asn Glu Ile Arg Ser Ala Cys Leu Pro Lys Pro Asp Glu Pro
1               5                   10                  15

Val Pro Leu

<210> SEQ ID NO 3
<211> LENGTH: 15
<212> TYPE: PRT
<213> ORGANISM: Artificial sequence
<220> FEATURE:
<223> OTHER INFORMATION: Translated from synthetic DNA
```

-continued

<400> SEQUENCE: 3

Tyr Gln Gly Gly Arg Gly Ser Asp Val Leu Arg Ile Ala Glu Met
1               5                   10                  15

<210> SEQ ID NO 4
<211> LENGTH: 15
<212> TYPE: PRT
<213> ORGANISM: Artificial sequence
<220> FEATURE:
<223> OTHER INFORMATION: Translated from synthetic DNA

<400> SEQUENCE: 4

Val Leu Arg Ile Ala Glu Met Lys Pro Leu Pro Lys Asp Glu Cys
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: Translated from synthetic DNA

<400> SEQUENCE: 5

Pro Leu Pro Lys Asp Glu Cys Arg Ile Lys Pro Glu Glu His Ala
1               5                   10                  15

<210> SEQ ID NO 6
<211> LENGTH: 15
<212> TYPE: PRT
<213> ORGANISM: Artificial sequence
<220> FEATURE:
<223> OTHER INFORMATION: Translated from synthetic DNA

<400> SEQUENCE: 6

Gly Val Asp Arg Ser Ala Thr Cys Gln Gly Asp Ser Gly Gly Pro
1               5                   10                  15

<210> SEQ ID NO 7
<211> LENGTH: 15
<212> TYPE: PRT
<213> ORGANISM: Artificial sequence
<220> FEATURE:
<223> OTHER INFORMATION: Translated from synthetic DNA

<400> SEQUENCE: 7

Val Val Cys Leu Lys Asn Asn Lys Ala Thr Leu Tyr Gly Ile Val
1               5                   10                  15

<210> SEQ ID NO 8
<211> LENGTH: 17
<212> TYPE: PRT
<213> ORGANISM: Artificial sequence
<220> FEATURE:
<223> OTHER INFORMATION: Translated from synthetic DNA

<400> SEQUENCE: 8

Pro Pro Thr Cys Gly Asp Ala Arg His Ser Val Lys Phe Ala Lys Val
1               5                   10                  15

Pro

<210> SEQ ID NO 9
<211> LENGTH: 12
<212> TYPE: PRT
<213> ORGANISM: Artificial sequence
<220> FEATURE:

<223> OTHER INFORMATION: Translated from synthetic DNA

<400> SEQUENCE: 9

Ile Gln Asp Thr Ala Arg Ser Ile Asp Ser Thr Val
1               5                   10

<210> SEQ ID NO 10
<211> LENGTH: 26
<212> TYPE: DNA
<213> ORGANISM: Artificial sequence
<220> FEATURE:
<223> OTHER INFORMATION: Synthetic DNA

<400> SEQUENCE: 10
taacgaattc gaaaattctc ctgaag                                        26

<210> SEQ ID NO 11
<211> LENGTH: 25
<212> TYPE: DNA
<213> ORGANISM: Artificial sequence
<220> FEATURE:
<223> OTHER INFORMATION: Synthetic DNA

<400> SEQUENCE: 11
gacgctcgag ttacttagaa aagtg                                         25

<210> SEQ ID NO 12
<211> LENGTH: 27
<212> TYPE: DNA
<213> ORGANISM: Artificial sequence
<220> FEATURE:
<223> OTHER INFORMATION: Synthetic DNA

<400> SEQUENCE: 12
gctctagaat gagcagccat catcatc                                       27

<210> SEQ ID NO 13
<211> LENGTH: 27
<212> TYPE: DNA
<213> ORGANISM: Artificial sequence
<220> FEATURE:
<223> OTHER INFORMATION: Synthetic DNA

<400> SEQUENCE: 13
cccaagcttt aagaggtcat aaactac                                       27

<210> SEQ ID NO 14
<211> LENGTH: 26
<212> TYPE: DNA
<213> ORGANISM: Artificial sequence
<220> FEATURE:
<223> OTHER INFORMATION: Synthetic DNA

<400> SEQUENCE: 14
ccggaattca tgctctctct agtgat                                        26

<210> SEQ ID NO 15
<211> LENGTH: 30
<212> TYPE: DNA
<213> ORGANISM: Artificial sequence
<220> FEATURE:
<223> OTHER INFORMATION: Synthetic DNA

<400> SEQUENCE: 15
ccgctcgagt aacacagtag aatcaatgct                                    30

```
<210> SEQ ID NO 16
<211> LENGTH: 24
<212> TYPE: DNA
<213> ORGANISM: Artificial sequence
<220> FEATURE:
<223> OTHER INFORMATION: Synthetic DNA

<400> SEQUENCE: 16
ccggaattca tgactgcccg aagc                                              24

<210> SEQ ID NO 17
<211> LENGTH: 30
<212> TYPE: DNA
<213> ORGANISM: Artificial sequence
<220> FEATURE:
<223> OTHER INFORMATION: Synthetic DNA

<400> SEQUENCE: 17
ccgctcgagt aaagtgaatg atggatcatt                                        30

<210> SEQ ID NO 18
<211> LENGTH: 45
<212> TYPE: DNA
<213> ORGANISM: Artificial sequence
<220> FEATURE:
<223> OTHER INFORMATION: Synthetic DNA

<400> SEQUENCE: 18
ggtgttgacc gctctgcaac atgtcagggt gattctggtg gacca                       45
```

HYBRIDOMA CELL STRAIN AND MONOCLONAL ANTIBODY PRODUCED THEREFROM AGAINST SERINE PROTEASE OF *TRICHINELLA SPIRALIS* IN INTESTINAL STAGE AND APPLICATION THEREOF

TECHNICAL FIELD

The disclosure belongs to the technical field of prevention and treatment of *Trichinella spiralis* (*T. spiralis*), and specifically relates to a hybridoma cell strain and a monoclonal antibody produced therefrom against serine protease of *T. spiralis* in an intestinal stage and application thereof.

BACKGROUND

Trichinellosis mainly occurs in hosts who eat uncooked or half-cooked meat containing *T. spiralis*. The average incubation period of human trichinellosis is 2 weeks. The main symptoms of patients in an acute phase include fever, severe muscle pain, severe diarrhea, facial edema, eosinophilia and the like, the symptoms can last for several weeks and lead to body failure, and especially severe infection patients may experience severe damage to myocardium and brain and even death.

In view of the great threat and harm caused by *T. spiralis* to public health safety and human health, the World Organization for Animal Health (OIE) lists trichinellosis as a compulsory inspection and mandatory inspection disease for the first inspection of slaughtered animals and trichinellosis is even one of the typical diseases which can cause sudden public health events except for fulminating zoonosis. At present, a microscopy method (3 larvae/g meat) and a pooled sample digestion method (1 larva/g meat) which are relatively time-consuming, labor-intensive and low-sensitive are still used for detection of *T. spiralis*.

Scholars at home and abroad have conducted a lot of research on detection methods of *T. spiralis*, such as indirect fluorescent immunoassay, immunoenzyme staining assay, western blotting assay and enzyme-linked immunosorbent assay (ELISA). The enzyme-linked immunosorbent assay (ELISA) is the most commonly used immunological method for detecting infection of *T. spiralis* and has high sensitivity, and the detection limit can be as low as 1 larva per 100 g of muscle tissue. At present, the excretory secretory (ES) antigens of *T. spiralis* muscle larvae is the only standard antigens for serological antibody detection specified by OIE and the International Commission on Trichinellosis. However, ES antigens is complex in component, cumbersome to prepare, long in production cycle and uneven in batch quality, and there are serious diagnostic blind window (during this times the larvae have developed infective larvae, but the antibodies can not been detected) and cross-reaction problems, so that practical application of the ES antigens is hindered.

SUMMARY

Aiming at the technical problem of how to specifically diagnose trichinellosis, the disclosure provides a hybridoma cell strain deposited under an accession number of CGMCC No. 18317 in China General Microbiological Culture Collection Center.

The disclosure also provides a monoclonal antibody against the serine protease of *T. spiralis* in an intestinal stage, which is secreted by the hybridoma cell strain CGMCC No. 18317 above.

Further, the amino acid sequence of an antigenic epitope polypeptide recognized by the monoclonal antibody is set forth as SEQ ID NO:1.

The hybridoma cell strain of the disclosure can be used to prepare a reagent for diagnosing infection of *T. spiralis*, and the antigenic epitope polypeptide set forth as SEQ ID NO:1 of the disclosure can be used to prepare diagnosing antigen or a vaccine for preventing infection of *T. spiralis*.

Beneficial Effects of the Disclosure

Due to the advantages of high specificity for binding to antigens, good purity, high reproducibility, convenient quality control, good affinity and mass production, so that monoclonal antibodies are widely used in establishment of immunological detection methods. Therefore, screening of a hybridoma cell strain which can secrete a specific antibody against Ts-ZH68 protein and identification of a Ts-ZH68 protein-specific B cell epitope recognized by the monoclonal antibody secreted therefrom are of great significance in improvement of diagnostic methods of trichinellosis and development of subunit vaccines.

The monoclonal antibody prepared by the disclosure reacts specifically with a crude extract antigen of *T. spiralis* muscle larvae. Ts-ZH68 competition ELISA detection results showed that the monoclonal antibody Ts-ZH68-2A4-Ab secreted by the hybridoma cell strain ZH68-2A4 can compete with the positive serum of pigs infected with *T. spiralis* for binding to a Ts-ZH68 antigen.

The disclosure uses a peptide scanning technology to identify the Ts-ZH68 antigen B cell epitope recognized by Ts-ZH68-2A4-Ab, and determines that the Ts-ZH68-2A4-Ab recognition peptide is $^{222}$GVDRSATCQGDSGGP$^{236}$.

DETAILED DESCRIPTION

The serine protease Ts-ZH68 antigen of 3-day-old *T. spiralis* in an adult stage: By immunologically screening the cDNA expression library of *T. spiralis* 3 days after infection, a high-abundance and high-reactivity antigen protein named ZH68 is obtained. ZH68 protein belongs to serine protease according to informatics sequence analysis. ZH68 gene registration number: EU263332, and protein registration number: ABY60762.1. The disclosure shows through further immunoblotting that the prokaryotic expression recombinant ZH68 antigen can be recognized by the serum of pigs infected with *T. spiralis* at 15 days, 30 days and 60 days respectively, indicating that ZH68 is an ideal candidate antigen for serological detection of *T. spiralis* and can be used to improve serological detection methods.

In the disclosure, TRIZOL is used to extract the total RNA of *T. spiralis*, then Ts-ZH68 is cloned by using a reverse transcription technology, the cDNA is inserted into a prokaryotic expression vector pET28a, the prokaryotic expression vector pET28a is used for prokaryotic expression of a Ts-ZH68 gene, expressed Ts-ZH68 is subjected to gel cut purification to immunize BALB/c mice, and spleen cells of the mice are taken and fused with SP2/0 myeloma cells to prepare hybridoma cells. Affinity-purified recombinant Ts-ZH68 and muscle larval ES antigens are used as detection antigens, an indirect ELISA detection method is established to screen positive hybridoma cells, and finally a hybridoma cell strain, ZH68-2A4, for stable secretion of an anti-Ts-ZH68 protein monoclonal antibody is obtained. This cell strain is deposited in the China General Microbiological Culture Collection Center on Aug. 15, 2019, the deposit address is No. 3, No. 1 courtyard, Beichen West Road, Chaoyang District, Beijing, China, Institute of Microbiology, Chinese Academy of Sciences, and the strain accession number of deposit is CGMCC No. 18317. The main experimental materials and sources used in the disclosure are as follows:

1. Main reagents and medicines: Ni purification column HisTrapHP purchased from GE Co., USA; fetal bovine serum and 1640 culture medium purchased from Biological Industries Co.; HAT culture medium (50*), HT culture medium (50*) and antibody subclass identification kit purchased from Sigma Co.; Solpble TMB substrate Solution purchased from TIANGEN Co.; horseradish peroxidase (HRP) labeled goat anti-mouse IgG antibody purchased from Beijing Bioss Co.; pre-stained protein Marker purchased from Fermentas Co.; restriction endonucleases EcoRI and XhoI, reverse transcriptase, Ex Taq DNA polymerase and T4 DNA ligase purchased from TaKaRa (Dalian) Co., Ltd; ECL luminescent substrate purchased from Beijing Solarbio Co.

2. Experimental animals: 6-week-old BALB/c mice provided by Changchun Yisi Experimental Animal Technology Co., Ltd.

The technical scheme of the disclosure is described in detail below. The molecular biology experiment methods such as reverse transcription, PCR and enzymatic digestion involved in the following examples, unless otherwise specified, are performed in accordance with the instructions of corresponding product kits or conventional technical methods in the art.

Example 1 Prokaryotic Expression and Purification of Ts-ZH68 Protein

1. Primer design: According to the ZH68 gene sequence registered in Genbank (accession number: EU263332), PCR amplification primers are designed, and the sequences are as follows:

The template used for Ts-ZH68 gene amplification is AD3-stage adult worm cDNA, and the amplification primers are as follows:

```
TsZH68-F:
5'-TAACGAATTC gaaaattctcctgaag -3',
list is set forth as SEQ ID NO: 10;
and TsZH68-R:
5'-GACGCTCGAG ttacttagaaaagtg -3',
list is set forth as SEQ ID NO: 11.
```

The underlined parts are the introduced EcoRI and XhoI enzymatic digestion sites.

2. Extraction and reverse transcription of *Trichinella spiralis* T1 (*T. spiralis*) AD3-stage adult worm RNA Rats infected with *T. spiralis* muscle larvae for 3 days are dissected, the small intestines are dissected, washed with sterile physiological saline and placed on separating sieve filter cloth, the physiological saline is preheated to 37° C., the small intestines are immersed and incubated at 37° C. for 4 hours and washed with sterile physiological saline containing 2% double antibodies, the supernatant is discarded, and AD3-stage adult worm are harvested. The extracted total RNA is used for reverse transcription to synthesize cDNA, and the system is as follows:

| | |
|---|---|
| M-MLV 5* Reaction Buffer | 5.0 μl |
| dNTP Mixture | 1.0 μl |
| M-MLV RT | 1.0 μl |
| RNAase inhibitor | 0.5 μl |
| oligo dT$_{18}$ | 1.0 μl |

RNAase-free water is added to 25 μl,
the substances are uniformly mixed for a reaction at 42° C. for 1 hour. Products are stored at −20° C.

3. Construction of an expression vector: 3-day-old adult worm cDNA obtained after reverse transcription is used as a template for amplifying Ts-ZH68.

A PCR reaction system (50 μL) is as follows:

| | |
|---|---|
| 10*Ex Taq Buffer | 5 μL |
| 10 mM dNTPs | 1 μL |
| Ex Taq | 0.5 μL |
| 10 pM upstream primer | 2 μL |
| 10 pM downstream primer | 2 μL |
| cDNA template | 3 μL |
| Sterilized ddH$_2$O | 36.5 μL |

The reaction conditions are circulation of pre-denaturation at 95° C. for 5 minutes, at 95° C. for 45 seconds, at 55° C. for 45 seconds and at 72° C. for 45 seconds 30 times and final extension at 72° C. for 10 minutes. PCR products is recovered. The target gene Ts-ZH68 obtained after gel recovery and the prokaryotic expression vector pET28a are subjected to double enzymatic digestion separately, and an enzymatic digestion system is as follows:

| 10*H Buffer | 2 μL |
|---|---|
| EcoRI | 2 μL |
| XhoI | 2 μL |
| Target gene | 10 μL |
| Sterilized ddH$_2$O | 4 μL |

At the same time, the prokaryotic expression vector pET28a is subjected to double enzymatic digestion, and an enzymatic digestion system is as follows:

| 10*H Buffer | 2 μL |
|---|---|
| EcoRI | 2 μL |
| XhoI | 2 μL |
| pET28a vector | 10 μL |
| Sterilized ddH$_2$O | 4 μL |

The enzymatic digestion reaction systems are placed in a 37° C. water bath for standing still for 2 hours, and then gel recovery is carried out. The target gene after double enzymatic digestion is ligated with the pET28a vector, and the system is: 10*T$_4$DNA Ligase Buffer 1 target gene obtained after enzymatic digestion 4 pET28a obtained after enzymatic digestion 1.5 μL, T$_4$DNA ligase 1 μL and ddH$_2$O 2.5 μL. The substances are ligated overnight at 16° C. All ligation products are transformed into *E coli* DH5a competent cells, and a single colony is picked for PCR identification and sequencing. Positive recombinant plasmids are transformed into BL21 (DE3) competent cells.

4. BL21(DE3)-pET28a-Ts-ZH68 induced expression and gel cut purification

When 1 ml solution contained recombinant bacteria is added into 100 ml of an LB culture medium for shaking culture at 37° C. until OD600 nm is about 0.5-0.8, isopropyl β-D-1-thiogalactopyranoside (IPTG) is added to a final concentration of 1 mmol/L, and the solution is induced at 37° C. for 6-8 hours. An expression product is subjected to SDS-PAGE electrophoresis and purified by a gel cut method. A cut gel block is added into an appropriate amount of PBS and ground into crushed particles, which can be used to immunize mice.

5. BL21(DE3)-pET28a-Ts-ZH68 affinity purification

Figure 1:
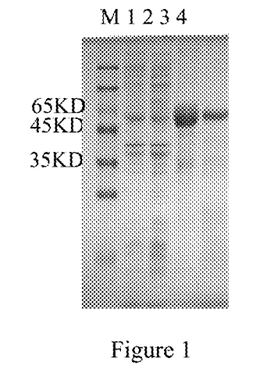
FIG. 1 shows SDS-PAGE analysis of Ts-Zh68 expression, M: protein molecular weight standard; 1: lysate of *E. coli* without pET-28a/Ts-Zh68 2: supernatant from lysate of recombinant *E. coli* carrying pET-28a/Ts-Zh68 after induction. 3: inclusion body from lysate of recombinant *E. coli* carrying pET-28a/Ts-Zh68 after induction; 4: purified recombinant ZH68 protein.

After induction, the bacterial solution is centrifuged and resuspended with 30 mL of a resuspension buffer (20 mM Tris-HCL, PH 8.0). The bacterial solution is subjected to an ice bath for 10 minutes and ultrasonic treatment on ice for a total of 30 minutes, wherein the ultrasonic treatment is performed for 3 seconds, then stops for 3 seconds, and so on. The bacterial solution is centrifuged at 8000 rpm for 10 minutes, and a precipitate is collected, resuspended with 30 ml of a pre-cooled inclusion body washing solution (2 M urea, 20 mM Tris-HCL, 0.3 M NaCL, PH 8.0) and subjected to an ice bath for 10 minutes and ultrasonic treatment on ice for a total of 10 minutes, wherein the ultrasonic treatment is performed for 3 seconds, then stops for 3 seconds, and so on. This step is repeated 3 times. The bacterial solution is centrifuged at 8000 rpm for 10 minutes, and a precipitate is collected, resuspended with 30 ml of a pre-cooled PBS washing solution (0.01 M PBS containing 4 M urea) and subjected to an ice bath for 10 minutes and ultrasonic treatment on ice for a total of 5 minutes, wherein the ultrasonic treatment is performed for 3 seconds, then stops for 3 seconds, and so on. This step is repeated twice. The bacterial solution is centrifuged at 8000 rpm for 10 minutes, and a precipitate is collected, resuspended with 5 ml of a binding buffer (8 M urea, 20 mM Tris-HCL, 0.3 M NaCL, 5 mM imidazole, pH 8.0) and dissolved overnight at 4° C. The bacterial solution is centrifuged at 8000 rpm for 30 minutes, and a supernatant is collected and filtered for sample loading. Ts-ZH68 with a His tag is purified by using an AKTA purifier 100 (GE Healthcare, USA) purification system. Elution Buffers containing 30 mmol/L, 50 mmol/L, 100 mmol/L and 300 mmol/L imidazole are used for elution separately, and purified recombinant ZH68 protein is subjected to SDS-PAGE analysis. It can be seen that the purified protein supernatant has only one clear and obvious band, and the size is consistent with the theoretical value (FIG. 1), indicating that a relatively pure rTs-ZH68 protein is obtained in this study. A BCA protein quantification kit is used for measuring the concentration of the purified protein, and the concentration of rTs-ZH68 protein is 0.85 mg/mL.

Example 2 a Preparation Method of a Hybridoma Cell Strain

1. Mouse Immunization

Five 6-week-old female BALB/c mice are immunized with the recombinant Ts-ZH68 protein obtained after gel cut purification in Example 1 every two weeks for a total of 4 times, the immunization dosage is 50 μg/mouse an equal volume of adjuvant added, Freund's complete adjuvant is used for the first immunization, Freund's incomplete adjuvant is used for the other three times, and the immunation route is intraperitoneal immunization.

One week after the third immunization and the fourth immunization, mice are tail-cleaved to collect blood, the serum is separated (4° C., centrifugation at 3000 rpm for 30 minutes), and the antibody level is detected by an affinity-purified Ts-ZH68-indirect ELISA method. The operation of the Ts-ZH68 indirect ELISA method is as follows: the recombinant Ts-ZH68 protein is diluted with a coating solution (0.1 M carbonate buffer, pH 9.6, Na$_2$CO$_3$ 63.6 g, NaHCO$_3$33.6 g, constant volume to 1000 mL), and the coating quantity is 0.1 μg/well and 100 μl per well. The recombinant Ts-ZH68 protein is coated at 37° C. for 1 hour and then placed overnight at 4° C. Afterwards, a plate is washed 3 times with PBST (containing 0.05% Tween 20). A blocking solution (5% skim milk) is used for blocking at 37° C. for 2 hours. Afterwards, the plate is washed 3 times with PBST. The serum to be tested is subjected to doubling dilution (or diluted with the hybridoma supernatant at a ratio of 1:2) and then added into a microwell plate with 100 μl per well. The serum is incubated at 37° C. for 1 hour. Afterwards, the plate is washed 3 times with PBST. A goat anti-mouse secondary antibody is diluted at a ratio of 1:1000 and incubated at 37° C. for 30 minutes. Afterwards, the plate is washed 4 times with PBST. Color development is carried out at 37° C. for 10 minutes. A reaction is stopped with 2 M H$_2$SO$_4$, and the absorbance at OD450 nm is read.

Three days before cell fusion, BALB/c mice with good immune effects are subjected to boosted immunization, and each mouse is injected intravenously with 50 μg of immunogen at the tail vein.

2. Cell Fusion

One day before fusion, mouse feeder layer cells are prepared, and BALB/c mouse peritoneal macrophages are taken according to a conventional method and spread in a 96-well cell culture plate for use. Three days after boosting, mice were sacrificed and the spleens are aseptically taken, the spleen cells are separated. $1*10^8$ spleen cells are mixed with $2.5*10^7$ SP2/0 myeloma cells at a ratio of 4:1 for cell fusion with 1 ml of PEG1000, and dropping ends within 1 minute. 1 ml of a 1640 culture medium preheated to 37° C. is then added dropwise into a cell suspension within 1 minute while stirring. 1 ml of the 1640 culture medium preheated to 37° C. is added dropwide into the cell suspension within 3 minutes while stirring. Finally, 10 ml of the 1640 culture medium at 37° C. is slowly added into the cell suspension, and the whole process is operated in a 37° C. water bath. The cell suspension is centrifuged at 1000 r/min for 10 minutes, the supernatant is discarded, and the cells are resuspended with an HAT culture medium, spread evenly on a 96-well cell culture plate pre-spread with feeder cells, and placed in a 5% $CO_2$ incubator for culture at 37° C.

3. Screening and Cloning of Positive Hybridoma Cell Strains

The Ts-ZH68 indirect ELISA method is used to screen positive hybridoma cell strains, positive hybridoma cells are subjected to expanded culture, and the positive hybridoma cells are subcloned for the first time by using a limiting dilution method. With reference to the ES indirect ELISA method described in OIE Terrestrial Manual 2017 Chapter 2.1.20-Trichinellosis to screen the positive hybridoma cell strains again, the positive hybridoma cells are subjected to expanded culture, the positive hybridoma cells are the subcloned by using a limiting dilution method at least 3 times, and subcloned positive hybridoma cells are frozen and stored in time. A hybridoma cell strain, ZH68-2A4, for stable secretion of an anti-Ts-ZH68 protein monoclonal antibody is obtained. This cell strain is deposited in the China General Microbiological Culture Collection Center on Aug. 15, 2019, the address is No. 3, No. 1 courtyard, Beichen West Road, Chaoyang District, Beijing, Institute of Microbiology, Chinese Academy of Sciences, the strain accession number of deposit is CGMCC No. 18317, and the monoclonal antibody secreted therefrom is named ZH68-2A4-Ab, hereinafter referred to as 2A4.

Example 3 Preparation of Anti-Ts-ZH68 Protein Monoclonal Antibody Ascites

Figure 2:
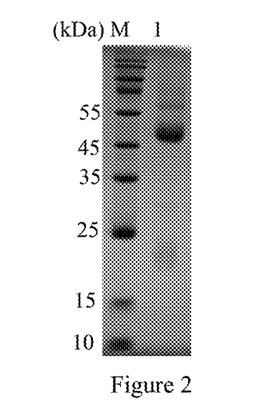
FIG. 2 shows SDS-PAGE analysis of a monoclonal antibody, M: protein relative molecular mass; 1: monoclonal antibody 2A4.

Each 12-week-old healthy BALB/c mouse is injected with 0.5 ml of paraffin oil intraperitoneally and $1*10^6$ hybridoma cells prepared in Example 2 intraperitoneally one week later, and after 7-10 days, when the abdominal cavity of each mouse is extremely dilated, ascites is extracted once every 2 days and then collected. The ascites is purified by using a protein G affinity chromatography medium. Before purification, the ascites is centrifuged at 10,000 rpm/min for 10 minutes to remove red blood cells and fat, and the supernatant is collected for purification. First, a chromatography column is connected with a syringe by an adapter, 5-10 ml of a binding buffer is injected into the chromatography column at a flow rate of 1 mL/min, the prepared ascites is injected into the chromatography column, the column is washed with 10-15 mL of a washing buffer to elute contaminant protein, and finally the column is eluted with 5 mL of an elution buffer, the solution is collected in a centrifuge tube, and SDS-PAGE analysis (FIG. 2) confirms that the monoclonal antibody 2A4 is successfully purified and stored at −20° C. for use.

Identification of a Monoclonal Antibody:

1. Subclass Identification of a Monoclonal Antibody

The monoclonal antibody obtained in Example 2 is subjected to subclass identification according to the operating instructions of an antibody subclass identification kit. The results show that the heavy chain of the monoclonal antibody 2A4 of the disclosure is IgG2a, and the light chain is kappa chain.

TABLE 1

| Subclass identification of the monoclonal antibody | | | | | | | | |
|---|---|---|---|---|---|---|---|---|
| Monoclonal antibody name | IgG1 | IgG2a | IgG2b | IgG3 | IgM | IgA | κ chain | λ chain |
| ZH68-2A4-Ab | 0.313 | 1.312 | 0.271 | 0.306 | 0.293 | 0.305 | 0.841 | 0.302 |

2. A Ts-ZH68 Competition ELISA Test

The coating and blocking method is the same as the Ts-ZH68 indirect ELISA method described in Example 2. From 1:1, the negative serum and positive serum of pigs infected with *T. spiralis* are subjected to twice doubling dilution, 50 µl of the diluted serum to be tested is taken separately and mixed with 50 µl of the anti-ZH68 monoclonal antibody supernatant in equal volume, 100 µl of a mixed solution is added into a microwell plate for reaction at 37° C. for 1 hour, and the remaining steps are the same as those of indirect ELISA to analyze whether the monoclonal antibody supernatant can compete with the positive serum of pigs infected with *T. spiralis* for binding to the Ts-ZH68 antigen.

Figure 3:
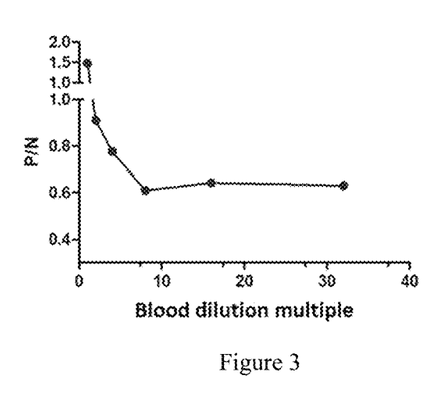
FIG. 3 shows results of competition between *Trichinella* positive serum and monoclonal antibody supernatant, the abscissa is the blood dilution multiple, and the ordinate is P/N (the ratio of positive serum to negative serum)

The test results confirm that the monoclonal antibody 2A4 prepared by the disclosure can compete with the positive serum of pigs infected with *T. spiralis* for binding to the Ts-ZH68 protein, as shown in FIG. 3.

TABLE 2

ELISA test results of the 2A4 monoclonal antibody competing with the positive serum of pigs infected with *T. spiralis* for binding to Ts-ZH68 antigen

| ZH68-2A4-Ab monoclonal antibody group | Quality control serum dilution ratio | | | | | |
|---|---|---|---|---|---|---|
| | 1:1 | 1:2 | 1:4 | 1:8 | 1:16 | 1:32 |
| Absorbance (P) of positive quality control serum at OD450 nm | 2.1360 | 1.7380 | 1.6450 | 1.2610 | 1.2520 | 1.0470 |

TABLE 2-continued

ELISA test results of the 2A4 monoclonal antibody competing with the positive
serum of pigs infected with *T. spiralis* for binding to Ts-ZH68 antigen

| ZH68-2A4-Ab monoclonal antibody group | Quality control serum dilution ratio | | | | | |
|---|---|---|---|---|---|---|
| | 1:1 | 1:2 | 1:4 | 1:8 | 1:16 | 1:32 |
| Absorbance (P) of negative quality control serum at OD450 nm | 1.4440 | 1.9090 | 2.1170 | 2.0690 | 1.9510 | 1.6620 |
| P/N value (the ratio of positive serum to negative serum) | 1.479224 | 0.910424 | 0.777042 | 0.609473 | 0.641722 | 0.629963 |

3. Western Blot Identification

Figure 4:
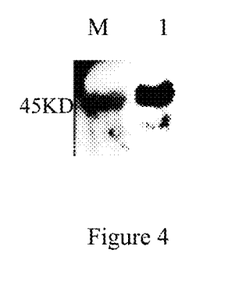
FIG. 4 shows western blot analysis of a soluble antigens of larva recognized by an anti-Ts-ZH68 monoclonal antibody to e, M: protein molecular mass standard; 1: soluble antigens of larva recognized by Ts-Zh68-2A4 monoclonal antibody.

*T. spiralis* muscle larvae are washed 3 times with ddH$_2$O, a small amount of ddH$_2$O is added, the larvae are ground into fragments with a tissue grinder in an ice bath, and then the larva fragments are crushed with an ultrasonic cell crusher in an ice bath. The larva fragments are subjected to ultrasonic treatment at a voltage of 300 V for 5 seconds at an interval of 9 seconds 5 times in 3 cycles, when it is observed under a light microscope that the larvae are crushed into small fragments, the larvae are subjected to alternate freezing and thawing at 4° C. and −20° C. 5 times, the larvae after freezing and thawing are centrifuged at 1600 g for 30 minutes at 4° C., and the supernatant is collected to obtain a soluble antigen. After treatment, SDS-PAGE is carried out, then the protein is transferred to a nitrocellulose membrane by electrotransfering, the membrane is blocked with 5% skim milk at 4° C. overnight, the monoclonal antibody is added for incubation at room temperature for 1 hour, and the membrane is washed with PBST 3 times, then incubated with a 3000-fold diluted HRP-labeled goat anti-mouse IgG antibody at room temperature for 1 hour, washed with PBST 3 times and then developed with an ECL luminescent substrate. The test results confirm that the monoclonal antibody 2A4 prepared by the disclosure can specifically react with a soluble antigen of *T. spiralis* muscle larvae, as shown in FIG. 4.

Example 4 Identification of B Cell Epitope Polypeptide

1. Segmented Expression of Ts-ZH68 Protein

Figure 5:
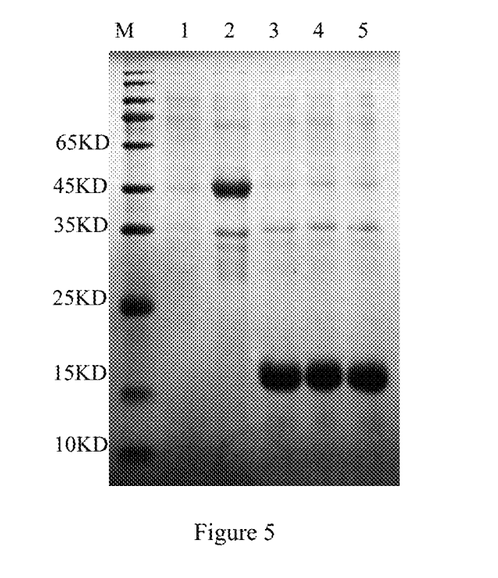
FIG. 5 shows SDS-PAGE analysis of segmented expression of Ts-ZH68 protein, 1: lysate of *E. coli* BL21 with pET-28a after induction; 2: lysate of *E. coli* BL21 with BL21-pET28a-ZH68 after induction; 3: lysate of *E. coli* BL21 with BL21-pET28a-ZH68-1 after induction; 4: lysate of *E. coli* BL21 with BL21-pET28a-ZH68-2 after induction; 5: lysate of *E. coli* BL21 with BL21-pET28a-ZH68-3 after induction.
Figure 6:
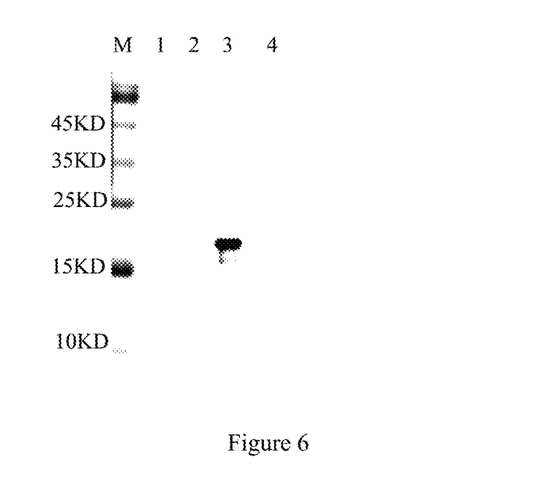
FIG. 6 shows western blot analysis of segmented expression of Ts-ZH68 protein, M: protein relative molecular mass; 1: reaction of mAbs Ts-Zh68-2A4 and lysate of *E. coli* BL21 with pET-28a after induction; 2: reaction of mAbsTs- Zh68-2A4 and lysate of *E. coli* BL21 with pET28a-Ts-Zh68-1 after induction; 3: reaction of mAbsTs-Zh68-2A4 and lysate of *E. coli* BL21 with pET28a-Ts-Zh68-2 after induction; 4: reaction of mAbs Ts-Zh68-2A4 and lysate of *E. coli* BL21 with pET28a-Ts-Zh68-3 after induction.
Figure 7:
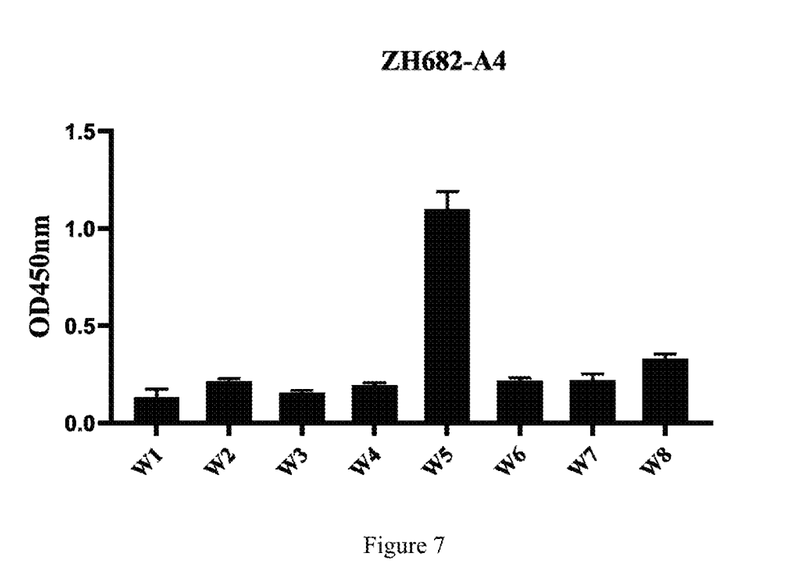
FIG. 7 shows ELISA analysis results, the abscissa is different peptide fragments, and the ordinate is OD values.

The gene sequence of the recombinant plasmid pET28a-ZH68 is used as a template, 3 pairs of primers are designed, ZH68-1-up and ZH68-1-down are used for amplification of Ts-ZH68-1, ZH68-2-up and ZH68-2-down are used for amplification of Ts-ZH68-2, and ZH68-3-up and ZH68-3-down are used for amplification of Ts-ZH68-3. After PCR amplification, the primers are connected to pET28a to construct recombinant plasmid and named pET28a-ZH68-1, pET28a-ZH68-2 and pET28a-ZH68-3 respectively. The recombinant bacterial containing pET28a-ZH68-1, pET28a-ZH68-2 and pET28a-ZH68-3 are subjected to induced expression separately according to the method in Example 1, and subjected to SDS-PAGE electrophoresis analysis to confirm the successful expression of short peptides (FIG. 5). SDS-PAGE is carried out after treatment of three segments of proteins, and the three segments of proteins are separately subjected to a western blot test with the monoclonal antibody according to the method in Example 3. SDS-PAGE analysis shows that all three proteins are successfully expressed. It is identified by western blot that the monoclonal antibody can react specifically with Ts-ZH68-2 and has high reactivity. The test results show that the B cell epitope targeted by the monoclonal antibody is located on the pET28a-ZH68-2 segmented protein (FIG. 6).

```
ZH68-1-up
5'-GCTCTAGAATGAGCAGCCATCATCATC-3',
list is set forth as SEQ ID NO: 12

ZH68-1-down
5'-CCCAAGCTTTAAGAGGTCATAAACTAC-3',
list is set forth as SEQ ID NO: 13

ZH68-2-up
5'-CCGGAATTCATGCTCTCTCTAGTGAT-3',
list is set forth as SEQ ID NO: 14

ZH68-2-down
5'-CCGCTCGAGTAACACAGTAGAATCAATGCT-3',
list is set forth as SEQ ID NO: 15

ZH68-3-up
5'-CCGGAATTCATGACTGCCCGAAGC-3',
list is set forth as SEQ ID NO: 16

ZH68-3-down
5'-CCGCTCGAGTAAAGTGAATGATGGATCATT-3',
list is set forth as SEQ ID NO: 17
```

2. Identification of Monoclonal Antibody Epitope

The biological software DNAstar is used to predict the hydrophilicity and antigenicity of ZH68, the epitope prediction programs ABpred and Bepipred are used for epitope prediction, the following short peptides (Table 3) are synthesized by using a PepScan technology, and then an indirect ELISA test is carried out with the coating quantity of 0.25 µg/well. The results show that 2A4 reacts specifically with the Ts-ZH68-W5 peptide, it is inferred that the Ts-ZH68 protein B cell epitope recognized by 2A4 is initially located at $^{222}$GVDRSATCQGDSGGP$^{236}$ in combination with the western blot results, and a (W5 in Table 4) nucleic acid sequence:

```
GGTGTTGACCGCTCTGCAACATGTCAGGGTGATTCTGGTGGACCA,
list is set forth as SEQ ID NO: 18
```

TABLE 3

| Synthetic short peptides | |
|---|---|
| Short peptide | Sequence |
| W1 is set forth as SEQ ID NO: 2 | $^{154}$YNNEIRSACLPKPDEPVPL$^{172}$ |
| W2 is set forth as SEQ ID NO: 3 | $^{185}$YQGGRGSDVLRIAEM$^{199}$ |

TABLE 3-continued

Synthetic short peptides

| Short peptide | Sequence |
|---|---|
| W3 is set forth as SEQ ID NO: 4 | $^{193}$VLRIAEMKPLPKDEC$^{207}$ |
| W4 is set forth as SEQ ID NO: 5 | $^{201}$PLPKDECRIKPEEHA$^{215}$ |
| W5 is set forth as SEQ ID NO: 6 | $^{222}$GVDRSATCQGDSGGP$^{236}$ |
| W6 is set forth as SEQ ID NO: 7 | $^{237}$VVCLKNNKATLYGIV$^{251}$ |
| W7 is set forth as SEQ ID NO: 8 | $^{255}$PPTCGDARHSVKFAKVP$^{271}$ |
| W8 is set forth as SEQ ID NO: 9 | $^{277}$IQDTARSIDSTV$^{288}$ |

TABLE 4

ELISA analysis results

| Group (Absorbance at OD450 nm) | Synthetic short peptide | | | | | | | |
|---|---|---|---|---|---|---|---|---|
| | W 1 | W 2 | W 3 | W 4 | W 5 | W 6 | W 7 | W 8 |
| ZH68-2A4-Ab | 0.1131 | 0.2303 | 0.1689 | 0.2034 | 1.0860 | 0.2273 | 0.2007 | 0.315 |

In summary, a monoclonal antibody against Ts-ZH68 protein is prepared and identified in the disclosure. The monoclonal antibody of the disclosure and the Ts-ZH68 protein B cell epitope polypeptide recognized by the monoclonal antibody can be used to prepare a reagent or a vaccine for diagnosing or preventing infection of *T. spiralis*, laying the foundation for establishment of a serological diagnosis method of *T. spiralis*.

What is claimed is:

1. A hybridoma cell line, deposited under an accession number of CGMCC No.18317 in the China General Microbiological Culture Collection Center on Aug. 15, 2019, with its deposit address of No.3, No.1 courtyard, Beichen West Road, Chaoyang District, Beijing, China.

2. A monoclonal antibody produced by culturing the hybridoma cell line of claim 1, wherein the monoclonal antibody is against serine protease of Trichinella spiralis in an intestinal stage, and wherein the monoclonal antibody is secreted by the hybridoma cell line.

3. The monoclonal antibody according to claim 2, wherein the amino acid sequence of an antigenic epitope polypeptide recognized by the monoclonal antibody is set forth as SEQ ID NO:1.

4. A method, comprising adding the monoclonal antibody of claim 2 secreted by the hybridoma cell line to a diagnosis reagent for diagnosing infection of *Trichinella spiralis*.

* * * * *